Figure 1:
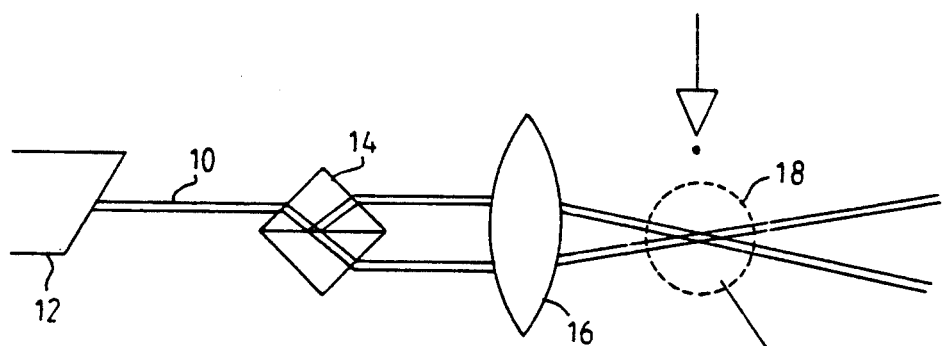

United States Patent [19]

Carr et al.

[11] Patent Number: 5,160,976
[45] Date of Patent: Nov. 3, 1992

[54] OPTICAL DETERMINATION OF VELOCITY USING CROSSED INTERFERENCE FRINGE PATTERNS

[75] Inventors: Robert J. G. Carr; David J. Clarke; Sumaia Al-Shukri, all of Wiltshire, England

[73] Assignee: Public Health Laboratory Service Board, London, United Kingdom

[21] Appl. No.: 727,428

[22] Filed: Jul. 9, 1991

Related U.S. Application Data

[63] Continuation of PCT/GB89/01336, Nov. 10, 1989, abandoned.

[30] Foreign Application Priority Data

Nov. 11, 1988 [GB] United Kingdom ............... 8826487

[51] Int. Cl.$^5$ .............................................. G01B 9/02
[52] U.S. Cl. .................................. 356/349; 356/28.5; 356/354; 356/336
[58] Field of Search ............... 356/349, 353, 354, 356, 356/336, 337, 338, 342, 343, 28.5

[56] References Cited

U.S. PATENT DOCUMENTS 3,897,152  7/1975  Farmer et al. ..................... 356/349
4,009,940  3/1977  Ohzu ................................. 356/354
4,148,585  4/1979  Bargeron et al. .................. 356/28.5
4,373,807  2/1983  Gouesbet .......................... 356/28.5

Primary Examiner—Samuel A. Turner
Attorney, Agent, or Firm—Browdy and Neimark

[57] ABSTRACT

Particle velocity is determined optically through the use of crossed interference fringe patterns. The fringe patterns are produced by passing laser beams of distinct wavelength along a common optical fibre and through two crossed diffraction gratings which are bonded to the free end of the fibre. Each diffraction grating is constructed in the manner of an interference filter so as to produce interference fringes at one wavelength but to transmit the other wavelength substantially uniformly across the grating. Other interference elements can be used in place of diffraction gratings and the use of a single diffraction grating is envisaged in certain circumstances. An indication of the sense of particle movement can be achieved by creating a fringe pattern of steadily increasing fringe spacing.

11 Claims, 4 Drawing Sheets

ASSYMETRICALLY SPACED GRATING

OPTICAL DETERMINATION OF VELOCITY USING CROSSED INTERFERENCE FRINGE PATTERNS

This is a continuation of PCT/GB89/01336 filed Nov. 10, 1989 and now abandoned.

This invention relates to methods and apparatus for the optical determination of particle velocity.

In the establised technique of laser Doppler Velocimetry (LDV), the particle whose velocity is to be determined is arranged to pass through an interference fringe pattern. If the particle passes orthogonally through fringes of fixed spacing, the rate of intensity fluctuations in the scattered light is a measure of particle velocity and can be accurately determined by, for example, correlation techniques. This use of a fringe pattern, as compared with single beam techniques, has the advantage of insensitivity to particle size.

In current LDV apparatus, the fringe pattern is typically formed by the recombination of a split laser beam at an angle which generates interference fringes at the point of intersection. The fringe plane is orthogonal to the plane of the crossed beams, and the particle flow is required to be normal to the fringe plane. Non-normal particle flow cannot be accommodated unless velocity measurements are made in the second (and possible third) dimension to permit vector analysis. This is currently achieved either by rotating a single optical system in two or three dimensions or by utilising a number of separate optical systems, one for each dimension. In the latter case, it has been proposed to utilize distinct wavelengths in the two or three dimensions so that light scattered from the respective fringe patterns can be distinguished. It is of course necessary for the two or three separate optical systems to be aligned so as to produce fringe patterns in a common measurement zone. hitherto, such LDV apparatus has been bulky and expensive. Scanning of particle velocities over a particular volume of interest has only been possible with cumbersome and time consuming experimental procedures. Thus, for example, in order to map particle flow velocity over a combustion chamber, it has been proposed to form an optically transparent model of the combustion chamber and to mount that model for incremental movement relative to the LDV apparatus as described above.

It is an object of one aspect of this invention to provide improved apparatus for the optical determination of particle velocity which is capable of supporting vector analysis in at least two dimensions, yet is inexpensive and physically compact.

Accordingly, the present invention consists in one aspect in apparatus for the determination of particle velocity, comprising means for generating two collinear beams of first and second distinct wavelengths; a first interference element disposed in the collinear beam path and adapted to form interference fringes at said first wavelength and to transmit or reflect said second wavelength substantially uniformly; a second interference element disposed in said collinear beam path and adapted to form interference fringes at said second wavelength and to transmit or reflect said first wavelength substantially uniformly, whereby, at least in measurement zone, two non-parallel interference fringe patterns are created; and detector means for the separate detection of light scattered from the respective interference patterns on passage of a particle through the measurement zone.

It should be underssood that the term "particle" herein is intended to encompass optical discontinuities in a flowing medium, such as gas bubbles in a liquid flow. Moreover the terms "optical" and "light" should not be regarded as restricting the apparatus to the visible spectrum.

Advantageously, the means for generating two collinear beams of first and second distinct wavelengths comprises a common optical fibre.

Preferably, the interference elements comprise respective diffraction gratings.

Suitably, the two diffraction gratings are mounted integrally with the optical fibre to form a probe.

According to a further aspect the present invention consist in an amplitude diffraction grating adapted to form interference fringes at a first wavelength and to pass a second and different wavelength substantially uniformly across the grating.

Advantageously the diffraction grating comprises an array of diffraction elements adapted to block light of said first wavelength and to transmit light of said second wavelength, with the diffraction elements preferably comprising interference filters.

Even in one dimension the use of a diffraction grating offers advantages over the conventional LDV approach of crossed beams. The apparent disadvantage of a grating, as compared to crossed beams, that the fringes are not confined to a defined measurement volume, is not believed to be of practical significance. The measurement volume can be adequately defined by the detector system.

Accordingly, the present invention consists in yet a further aspect in apparatus for the optical determination of particle velocity, comprising a diffraction grating for the production of interference fringes and detector means for detecting light scattered from the fringes on the passage of a particle, the detector means being arranged to detect ligth scattered from only a defined measurement zone within the fringe pattern.

Advantageously, the diffraction grating is bonded to the end of an optical fibre, suitably with appropriate lens means.

In a further aspect, the present invention consists in a method of determining optically particle velocity comprising generating two collinear beams of first and second distinct wavelengths along a beam path containing two interference elements each adapted to form interference fringes at one of said wavelengths and to transmit or reflect the other of said wavelengths substantially uniformly, thereby to create in a measurement zone two non-parallel interference fringe patterns; detecting light scattered from the respective interference patterns on passage of a particle through the measurement zone and determining through the frequency of intensity variation in the scattered light a component of said particle velocity in each of two orthogonal directions.

In another aspect, the present invention consists in a method for the optical determination of particle velocity, comprising detecting light scattered on passage of a particle through an interference fringe pattern, wherein the inter-fringe spacing of the fringe pattern increases across the fringe pattern and wherein the step of detecting light includes distinguishing between those amplitude modulation frequencies which increase and those which decrease with time, thereby to provide an indication of the sense of particle movement.

Figure 2:
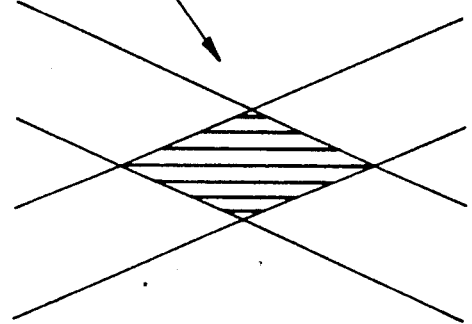
Figure 2:
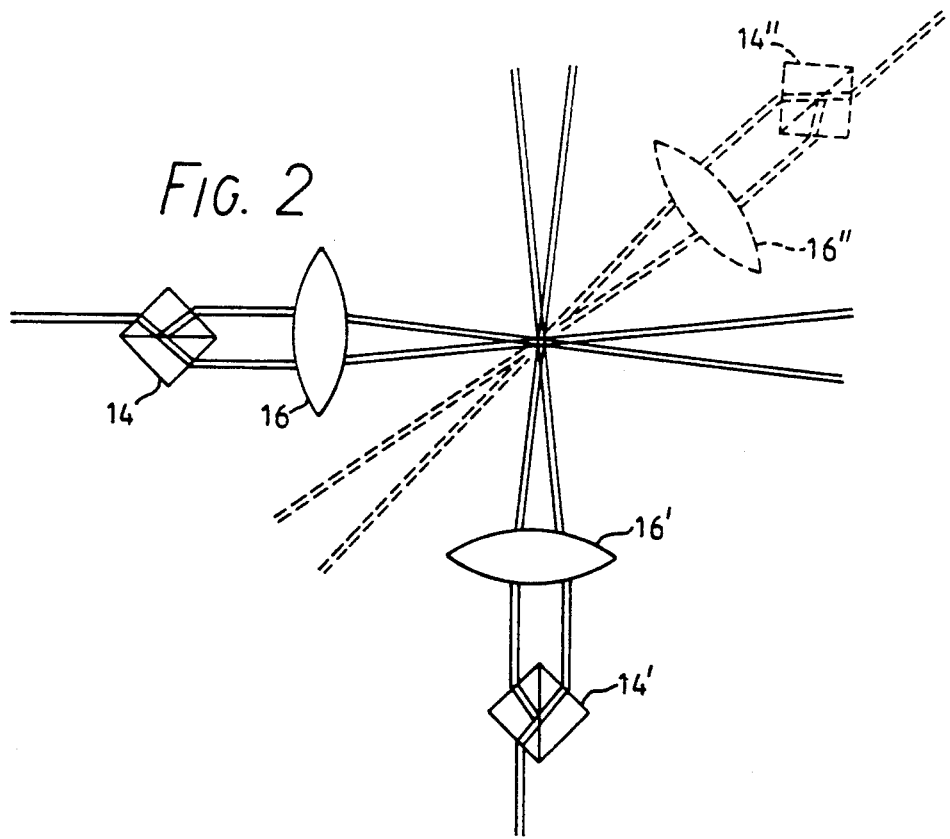
Figure 3:
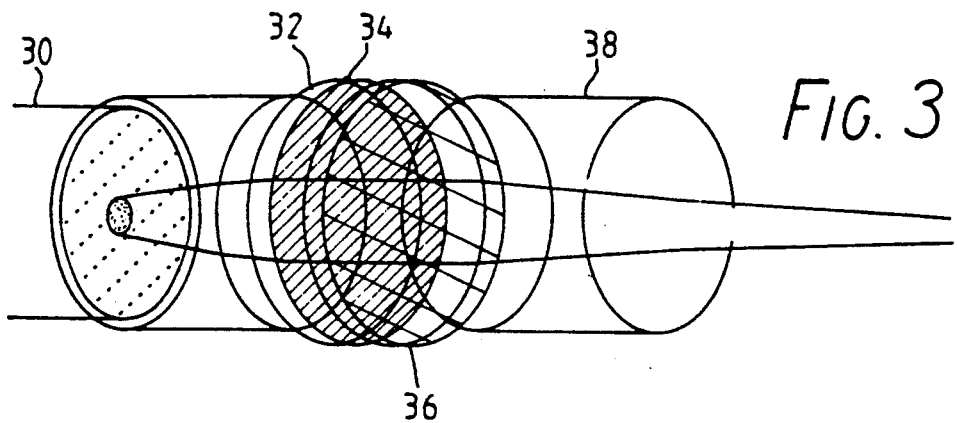
Figure 4A:
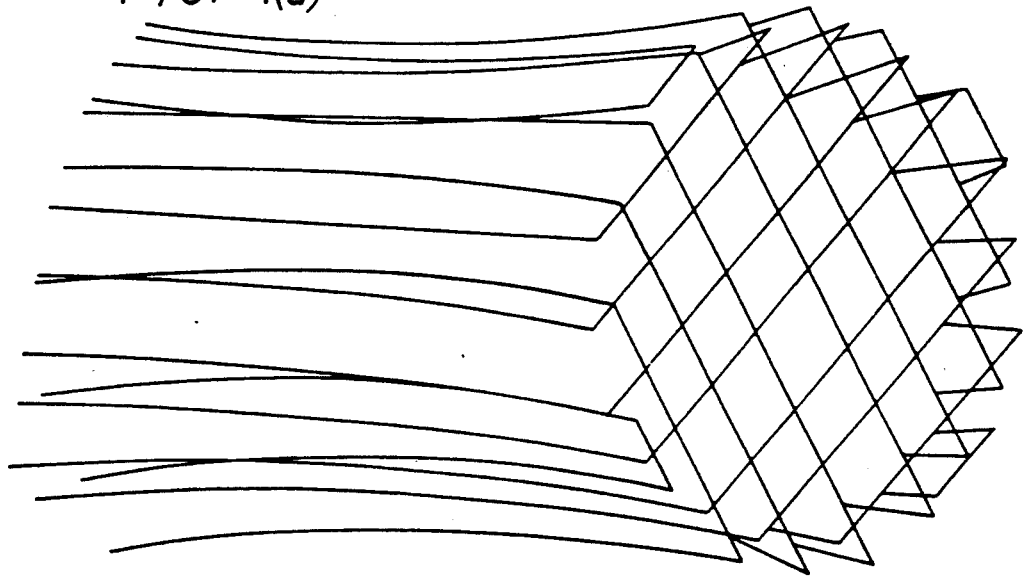
Figure 5A:
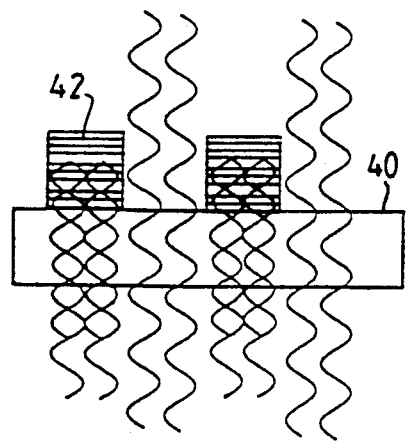
Figure 6:
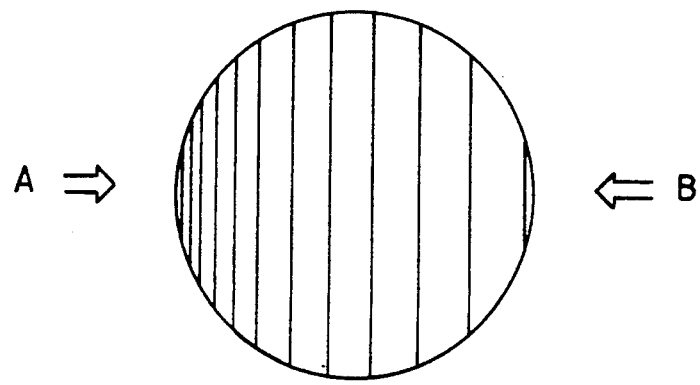
Figure 7A:
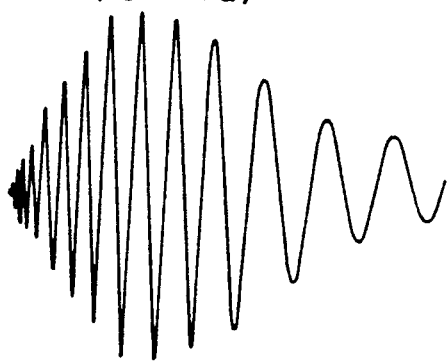
Figure 8:
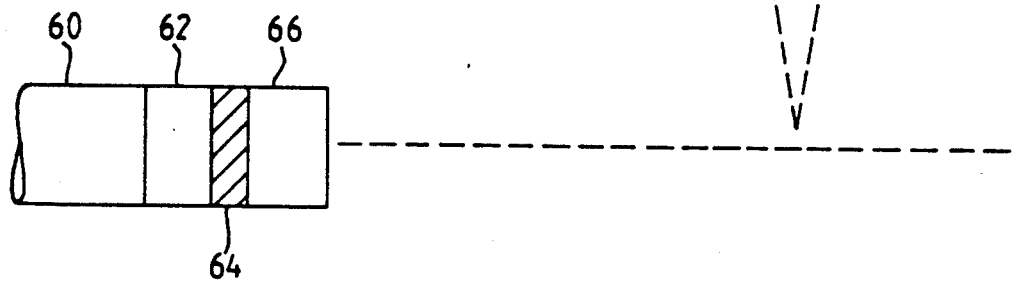

The invention will now be described by way of example with reference to the accompanying drawings in which:

FIG. 1 is a diagram illustrating conventional one dimensional LDV; FIG. 2 is a diagram illustrating conventional three dimensional LDV; FIG. 3 is a perspective view showing apparatus according to the present invention; FIGS. 4a) and 4b) are diagrams illustrating the fringe patterns produced by two variations of the apparatus of FIG. 3; FIGS. 5a) to 5f) are diagrams illustrating the formation of diffraction gratings in accordance with the present invention; FIG. 6 illustrates a modified figure pattern produced in apparatus according to a further embodiment of the invention; FIGS. 7a) and 7b) illustrate detected signals from apparatus utilising the fringe pattern of FIG. 6; and FIG. 8 illustrates a further embodiment of the present invention.

Conventional one dimensional Laser Doppler Velocimetry (LDV) is illustrated in FIG. 1. The beam 10, from a laser 12 is split in a beam-splitter 14 with the two beams being caused, trough a focussing lens 16, to intersect at a measurement zone 18. In this way a fringe pattern is established as illustrated diagramatically in the figure, with the fringes being normal to the particle velocity, illustrated by arrow 20. It would well be understood that by detecting light scattered from the fringe pattern on passage of a particle, the particle velocity can be determined. If it is desired to obtain simultaneous measures of velocity in more than one dimension, it is necessary to align two or three of the optical systems shown in FIG. 1 along respective axes as shown in FIG. 2. It has been proposed that in order to distinguish, in the detected light, between scatter from the two or three fringe patterns, light at different wavelengths be employed.

It will be recognised that, even if only two dimensions are covered, apparatus such as that illustrated in FIG. 2 is bulky and likely to be difficult to set up. This apparatus further does not lend itself to multi-point velocity determinations over a volume of interest.

Referring now to FIG. 3, there is shown a monomode optical fibre 30 provided with means (not shown) for launching into the fibre light of two distinct wavelengths $\lambda_1$ and $\lambda_2$. These can be from separate lasers or from a single, multi-line laser. There is bonded to the free end of the fibre 30 a SELFOC graded active index micro lens, this lens 32 in turn carrying a pair of crossed diffraction gratings 34,36. Finally, there is provided a further micro lens 38. The lens 32 serves to provide a collimated beam whilst lens 38 brings the output of the diffraction gratings into focus.

Each of the diffraction gratings is of a special form. It will be understood that a conventional diffraction grating may typically comprise a series of transparent parallel regions in a block which is otherwise opaque. These may, for example, be formed by etching grooves through an opaque layer. The conventional grating operates to diffract light over a broad range of wavelengths, although the diffraction is of course wavelength dependent. In a diffraction grating according to the present invention, however, it is arranged that interference fringes are formed in light of a first wavelength whereas light of a second wavelength passes substantially uniformly through the diffraction grating. The second beam thus retains its Gaussian amplitude distribution. Referring to FIG. 3, diffraction grating 34 operates to form interference fringes in the light $\lambda_1$ but passes light of wavelength $\lambda_2$ substantially unhindered. The diffraction grating 36 passes light of wavelength $\lambda_1$ (with its now formed interference fringes) substantially unhindered but forms interference firnges in the light of wavelength $\lambda_2$. Since the two diffraction gratings 34 and 36 are crossed, that is to say the parallel lines in one grating are orthogonal to the lines of the other grating, the interference fringe patterns at the two wavelengths are also orthogonal. This is illustrated in FIG. 4a).

Techniques known from conventional LDV can be employed to detect and correlate light scattered from the described orthogonal fringe system. To define a small measuring volume, it is often preferable to position a suitably focussed detector or detectors orthogonally of the beam path. In other applications, where the definition of a small scattering volume is not regarded as important, it would be possible to detect scattered light along the beam path; thus the same optical fibre could be used for both illumination and detection.

Examples of the formation of diffraction gratings according to the invention will now be described with reference to FIGS. 5a)–5f).

Figure 5B:
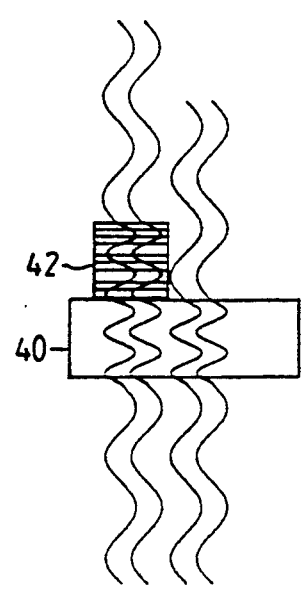

In FIG. 5a), there is shown—in section—a substrate 40 onto which are deposited parallel strips 42 of an interference filter which is designed to block wavelength $\lambda_1$ but pass wavelength $\lambda_2$. The design of such filters from multi-layer stacks of defined refractive index and thickness is a well-established technique requiring no further elaboration. The parallel strips may be formed, for example, by ion beam etching of grooves in a continuous interference filter layer deposited on the substrate. At wavelength $\lambda_1$, this diffraction grating will act in essentially conventional manner to form interference fringes. Since the strips 42 are transparent at wavelength $\lambda_2$, however, light of wavelength $\lambda_2$ will pass substantially unhindered through the diffraction grating. In one example, a strip width of 10 $\mu$m is employed with an equal spacing of 10 $\mu$m between strips. Care must of course be taken to avoid phase effects. It will be recognised that whereas light of wavelength $\lambda_2$ will be transmitted both through the strips 42 and through the regions between the strips, the optical path length in these two cases may be different. This problem is illustrated in FIG. 5b).

Figure 5C:
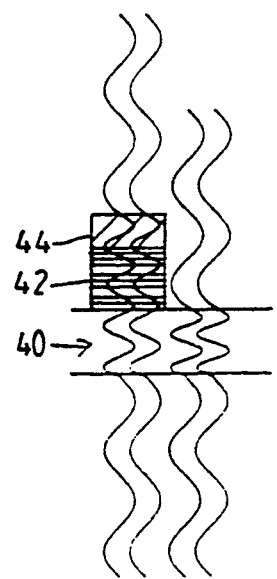
Figure 5D:
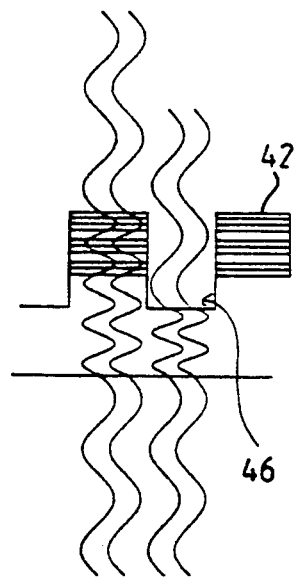

One method of dealing with the problem of phase mis-match is to deposit on top of the strips 42, an element 44 of appropriate thickness and refractive index to re-establish phase. This is illustrated in FIG. 5c). The element 44 can of course be formed by the deposition of a continuous layer over the interference filter layer, before the strips are etched. An alternative, illustrated in FIG. 5d) is to continue the etching process so as to form grooves 46 in the substrate between the strips 42. With a groove of appropriate depth, phase can again be re-established.

The second diffraction grating 26 can be produced with identical techniques, using an interference filter material that blocks light of wavelength $\lambda_2$ but transmits light of wavelength $\lambda_1$.

Figure 5E:
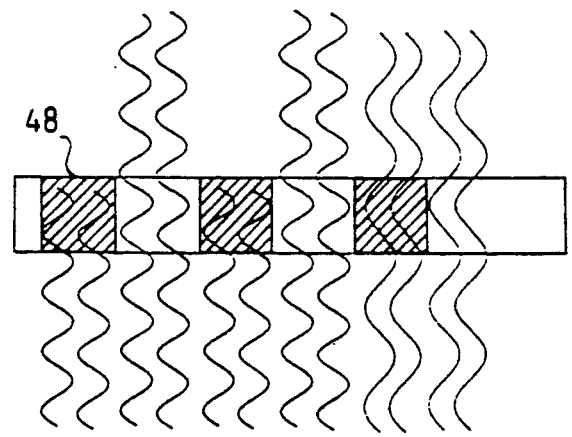

An alternative to the use of strips of interference filter material is illustrated in FIG. 5e). In this case, the diffraction grating is of uniform thickness but has within it linear regions 48 that block one wavelength but transmit the other. The remainder of the grating is transparent to both wavelengths. The selectively absorbing regions can be produced in a variety of ways apparent to the skilled man.

Figure 5F:
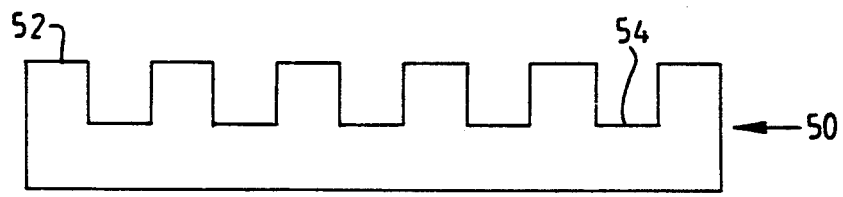
Figure 5F:
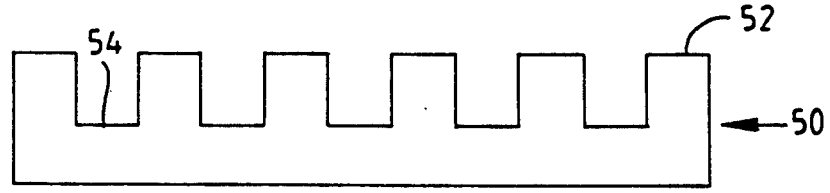

It will be possible within the compass of the present invention to employ transmission phase rather than amplitude diffraction gratings. Thus, referring to FIG. 5f), each grating 50 is formed of optical glass with flats 52 separated by lands 54. The physical spacing between the flats 52 and the lands 54, is selected—together with the refractive index of the glass to introduce a phase difference of $\pi$ at one of the wavelengths and $2\pi$ at the other. Thus one grating introduces a phase difference of $\pi$ at $\lambda_1$, and thus creates interference fringes, and a phase difference of $2\pi$ at the other wavelength $\lambda_2$, which is accordingly transmitted without perturbation. The other grating, having a different flat/land spacing, or using glass of a different refractive index or a combination of these, introduces a phase difference of $2\pi$ at $\lambda_1$, and thus transmits the fringes unperturbed but creates interference in $\lambda_2$ through the introduction of a $\pi$ phase difference.

Still further approaches will occur to the skilled man for producing a diffraction grating which forms interference fringes in light of wavelength $\lambda_1$ whilst transmitting light of wavelength $\lambda_2$ substantially uniformly. In appropriate cases, it would be possible to form such gratings in the form of reflection gratings and these are encompassed within the present invention. It will also be possible to utilise elements other than diffraction gratings to produce interference fringes in the two collinear beams. Two Youngs slits could be employed, for example, each formed in a substrate which is transparent at one wavelength and opaque at the other. Still other forms of interference elements will occur to the skilled man.

In order to provide a measure of particle velocity in the third dimension, that is to say parallel to the beam, it is proposed in a preferred form of this invention to utilise back scattered light from the particles, detected along the optical fibre. This Doppler shifted back scattered light is heterodyned with the illuminating light and a measurable beat frequency is detected. This can be performed with either of the wavelengths $\lambda_1$ and $\lambda_2$.

Unless the particle is moving in precisely the Z direction, that is to say parallel with the beam, the back scattered light will include frequencies associated with passage through the $\lambda_1$ or $\lambda_2$ fringes. These will usually be readily separable from the beat frequency of interest. An alternative, however is use a third frequency $\lambda_3$ for the Doppler shift determination of volocity in the Z direction. In for example an arrangement utilising:

$\lambda_1 = 633$ nm
$\lambda_2 = 488$ nm
$\lambda_3 = 830$ nm it can be arranged for $\lambda_3$ to be transmitted in substantially unchanged Gaussian profile through the interference elements which generate fringes in $\lambda_1$ and $\lambda_2$ respectively.

In many applications, it is important to determine not only the magnitude and directional line of a velocity but also the sense (polarity) of movement along that line. With conventional LDV techniques, the passage of a particle through the interference fringe pattern is characterised by a frequency "burst" which is broadly symmetrical along the time axis. There is accordingly an ambiguity in the sense (polarity) of the movement. It has been proposed previously that the frequency of the illuminating beam be modulated such that the fringe pattern established in the measuring volume is continuously moving. In this way, a frequency shift is created in the scattered light with the sense of the frequency shift being determined by the direction of movement of the fringe pattern (which is known at any one time) and the direction of movement of the particle. In accordance with the present invention, an improved technique is provided for determining the sense of particle velocity.

With reference to FIG. 6, it is now proposed that each fringe diffraction grating be formed with a spacing between adjacent lines which varies monotonically across the grating. This variation in spacing can be created in a number of ways, depending upon the method of construction of grating. In the case of a grating formed by ion beam etching, the position controller of the ion beam is adapted to increment the normally constant spacing between successive passes. In the case of etching techniques utilising an optical mask to define regions to be etched away, the usually planar mask may be deformed so that in the plane normal to the grating and normal to the lines within the grating, the mask has a radius of curvature which increases uniformly across the mask. In a still further alternative, optical techniques can be employed to produce the required mask pattern.

Figure 7B:
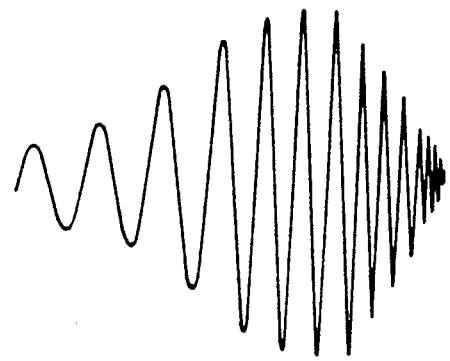

In the case of a particle passing through such a fringe pattern of graded inter-fringe spacing, the detected signal will be typically shown in FIG. 7a) if the direction of particle movement is in the sense of arrow A in FIG. 6 and as shown in FIG. 7b) in the case of movement in the direction of arrow B. Whilst the derivation of a measure for particle velocity is now less straightforward than in the case where the inter-fringe spacing is uniform, it becomes possible for the detection system to distinguish between particles of identical speed travelling in opposite directions. Thus the detection system is adapted to distinguish between bursts in which the rate of amplitude variation increases thoughout the burst or decreases.

It is recognised that even in one dimensional LDV the present invention offers advantage over conventional apparatus. In this case, aparatus as shown in FIG. 8 comprises an optical fibre 60, a graded refractive index collimating lens 62, a diffraction grating 64 and a focussing lens 66 of the same general construction as lens 62. Interference fringes are created and a detection zone is defined by focussed detector 68. The diffraction grating need not necessarily be of the form in which a particular wavelength is transmitted uniformly, but such an arrangement may be useful as outlined below.

Whilst the described arrangement lacks the facility of a rapid change in fringe pattern through a shift in angle of one of the two laser beams in conventional LDV apparatus, it is a straightforward matter to provide a small selection of optical fibre probes having different diffraction gratings.

The construction is compact and robust and lends itself to an arrangement in which remote probes are inverted into a reaction vessel or other environment inaccessible to bull optics LDV apparatus.

Figure 4B:
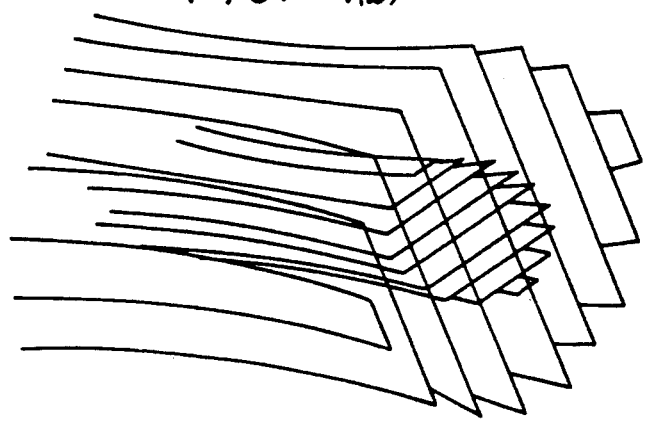

In a known system for investigating particles by light scattering (see for example U.S. Pat. No. 4,387,933), collinear beams of distinct wavelengths are employed, with detection of light from a broad, main beam being triggered by a narrow, trigger beam. In this way, scatter from a particle clipping the main beam—and thus failing to break the trigger beam—can be excluded. It has been proposed by the present applicants (WO88/01736) that these two beams be produced from a single optical fibre. By combining that technique with the present invention, apparatus can be produced which is capable simultaneously of LDV and, for example, particle sizing. In this variation, the lens 32 of the FIG. 3 embodiment is selected to have a degree of chromatic aberration such that the $\lambda_1$ and $\lambda_2$ beams are brought to focus at different points. This has the result that, in the measuring zone, the beams are of differing widths with, say, the narrower $\lambda_1$ beam serving as a trigger beam in the particle sizing mode. This arrangement is illustrated in FIG. 4b)

If, in a particular application, it is desired to combine particle sizing with one dimensional LDV, it would be advantageous to employ a single diffraction grating according to this invention. In this way a broad, main beam with interference fringes could be combined with a Gaussian trigger beam.

It should be understood that this invention has been described by way of example only, and a variety of further modifications may be made without departing from the scope of the invention. Thus be described arrangement in which interference fringes are formed throughout space could be replaced by an arrangement in which an image of the diffraction grating is formed at the measuring zone. The described arrangement in which the diffraction gratings are mounted at the end of an optical fibre to form a probe has many advantages. Thus, particle velocity can be determined at remote locations which do not lie in a "line of sight". It is possible, moreover, to multiplex a number of identical probes, either optically or electronically. Nevertheless other arrangements can be employed without departing from the scope of this invention. Thus separately mounted diffraction gratings could be used with an optical fibre and other focussing means beyond that specifically described and indeed the optical fibre could be replaced with other means for generating two collinear beams. As mentioned previously, interference elements other than diffraction gratings may in appropriate circumstances be employed.

We claim:

1. Apparatus for the optical determination of particle velocity, comprising means for generating two beams of first and second distinct wavelengths; a first interference element adapted to form interference fringes at said first wavelength, a second interference element adapted to form interference fringes at said second wavelength, whereby, at least in a measurement zone, two non-parallel interference fringe patterns are created; and detector means for the separate detection of light scattered from the respective interference patterns on passage of a particle through the measurement zone, characterised in that said two beams are collinear, in that the first and second interference elements are disposed in the collinear beam path, in that the first interference element is adapted to transmit or reflect said second wavelength substantially uniformly and in that the second interference element is adapted to transmit or reflect said first wavelength substantially uniformly.

2. Apparatus according to claim 1, wherein the means for generating two collinear beams of first and second distinct wavelengths comprises a common optical fibre.

3. Apparatus according to claim 1, wherein the interference elements comprise respective diffraction gratings.

4. Apparatus according to claim 3, wherein each diffraction grating comprises an array of diffraction elements adapted to block light of said first wavelength and to transmit light of said second wavelength.

5. Apparatus according to claim 4, wherein said diffraction elements comprise blocks of interference filter material.

6. Apparatus for the optical determination of particle velocity, comprising an interference element for the production of interference fringes and detector means for detecting light scattered from the fringes on the passage of a particle therethrough, characterised in that the interference element is a diffraction grating and in that the detector means is arranged to distinguish light scattered from a defined measurement zone within the fringe pattern.

7. Apparatus according to claim 6, wherein the diffraction grating is bonded to the free end of an optical fibre.

8. Apparatus according to claim 6, wherein said diffraction grating is adapted to form interference fringe at one wavelength and to transmit a different wavelength substantially uniformly.

9. A method of determining optically particle velocity comprising generating two beams of first and second distinct wavelength; using two interference elements each adapted to form interference fringes at one of said wavelengths to create in a measurement zone two non-parallel interference fringe patterns; detecting light scattered from the respective interference patterns on passage of a parricle through the measurement zone and determining through the frequency of intensity variation in the scattered light a component of said particle velocity in each of two orthogonal directions; characterised in that the two beams are collinear and in that each interference element is adapted to transmit or reflect substantially uniformly the other of said wavelengths.

10. A method for the optical determination of particle velocity, comprising detecting light scattered on passage of a particle through an interference fringe pattern, characterised in that the inter-fringe spacing of the fringe pattern increases across the fringe pattern and wherein the step of detecting light includes distinguishing between amplitude modulation frequencies which increase and decrease with time, thereby to provide an indication of the sense of particle movement.

11. A method according to claim 10, wherein said interference fringe pattern is formed by a diffraction grating the line spacing of which varies monotonically across the grating.

* * * * *